United States Patent

Tasaka et al.

[11] Patent Number: 5,843,950
[45] Date of Patent: Dec. 1, 1998

[54] 1,4-DIHYDROPYRIDINE COMPOUND AND PHARMACEUTICAL COMPOSITION CONTAINING THE SAME

[75] Inventors: Shigeyuki Tasaka, Saitama; Teruhisa Miura, Tokyo; Akira Kiue, Omiya; Taketsugu Seki, Omiya; Tetsuro Sano, Omiya; Mie Kamakura, Kitaadachi; Masakazu Fujita, Urawa, all of Japan

[73] Assignee: Nikken Chemicals Co., Ltd., Tokyo, Japan

[21] Appl. No.: 776,258

[22] PCT Filed: Jul. 28, 1995

[86] PCT No.: PCT/JP95/01507

§ 371 Date: Jun. 4, 1997

§ 102(e) Date: Jun. 4, 1997

[87] PCT Pub. No.: WO96/04268

PCT Pub. Date: Feb. 15, 1996

[30] Foreign Application Priority Data

Jul. 29, 1994 [JP] Japan .................................. 6-196204
Mar. 13, 1995 [JP] Japan .................................. 7-79331

[51] Int. Cl.$^6$ ................ C07D 401/12; C07D 401/14; A61K 31/445; A61K 31/495
[52] U.S. Cl. .................. 514/255; 514/332; 514/333; 544/357; 544/360; 546/256; 546/263
[58] Field of Search .................. 546/256, 263; 544/360, 357; 514/332, 333, 255

[56] References Cited

U.S. PATENT DOCUMENTS 4,876,255  10/1989  Franckowiak et al. ............ 514/252

FOREIGN PATENT DOCUMENTS

| 0 173 943 | 3/1986 | European Pat. Off. . |
| 0 287 866 | 10/1988 | European Pat. Off. . |
| 0 325 187 | 7/1989 | European Pat. Off. . |
| 61-60683 | 3/1986 | Japan . |
| 2-40383 | 2/1990 | Japan . |
| 2-240081 | 9/1990 | Japan . |
| 03176471 | 7/1991 | Japan . |
| 4-244081 | 9/1992 | Japan . |
| 5-117235 | 5/1993 | Japan . |
| 08040904 | 2/1996 | Japan . |

*Primary Examiner*—Alan L. Rotman
*Attorney, Agent, or Firm*—Finnegan, Henderson, Farabow, Garrett & Dunner, L.L.P.

[57] ABSTRACT

A 1,4-dihydropyridine compound having the formula (I):

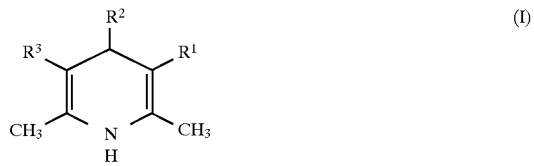

wherein, $R^1$ indicates —COO—A—(3-pyridyl), A indicates a $C_3$–$C_6$ straight chain alkylene group in which one piperazine may be interposed; $R^2$ indicates a $C_2$–$C_{10}$ alkyl group, alkenyl group or alkynyl group; a lower alkyl group or lower alkenyl group having a substituent; or a cycloalkyl group which may have a substituent; $R^3$ indicates the same group as $R^1$ or —COO—$R^4$; and $R^4$ indicates a lower alkyl group which may have a substituent or its pharmacologically acceptable salt and an anti-allergenic drug, antiphlogistic, drug for overcoming resistance to anti-cancer drugs, or drug for reinforcing the effect of anti-cancer drugs containing the same as effective ingredients.

9 Claims, No Drawings

1,4-DIHYDROPYRIDINE COMPOUND AND PHARMACEUTICAL COMPOSITION CONTAINING THE SAME

CROSS REFERENCE

This application is a 371 of PCT/JP95/01507 filed Jul. 28, 1995

TECHNICAL FIELD

The present invention relates to a novel 1,4-dihydropyridine compound having a platelet activating factor (PAF) antagonistic action and thromboxane synthesis inhibiting action and further having an action for overcoming resistance to an anti-cancer drug or an action for reinforcing the effect of an anti-cancer drug and an antiallergenic, antiphlogistic, a drug for overcoming resistance to an anti-cancer drug, or a drug for reinforcing the effect of an anti-cancer drug containing the said compounds or a pharmacologically acceptable salt thereof as an effective ingredient.

BACKGROUND ART 1,4-dihydropyridine derivatives have been reported to have many pharmacological activities, among which particularly the vasodilating action based on the calcium antagonistic action is widely known. Further, in addition to this vasodilating action, compounds having an action suppressing platelet aggregation are being developed with the intent of treatment of ischemic diseases (see Japanese Unexamined Patent Publication (Kokai) No. 61-197578, Japanese Unexamined Patent Publication (Kokai) No. 62-187468, and Japanese Unexamined Patent Publication (Kokai) No. 3-20271). As other actions, Japanese Unexamined Patent Publication (Kokai) No. 1-113367 reports a platelet activating factor (PAF) antagonistic action and Japanese Unexamined Patent Publication (Kokai) No. 61-167617 a thromboxane $A_2$ (Tx$A_2$) synthesis inhibiting action, but these are considered to suppress just PAF or Tx$A_2$ alone. Further, Japanese Examined Patent Publication (Kokoku) No. 56-37225 shows compounds having a coronary vasodilating action and describes a general formula which includes the compounds of the present invention, but this publication does not describe as specific compounds the compounds included in the present invention having the 3-(3-pyridyl) propyl group etc. at the 3-position of the 1,4-dihydropyridine.

Further, Japanese Unexamined Patent Publication (Kokai) No. 61-60683 shows compounds having a thromboxane synthesis inhibiting action and describes a general formula including the compounds of the present invention, but the publication does not describe as specific compounds any compounds with an isopropyl group or other $C_2$–$C_{10}$ alkyl group bonded at the 4-position of the 1,4-dihydropyridine. Further, the compounds described in the publication, as shown in the later test examples, have a Tx$A_2$ synthesis inhibiting action, but have no PAF antagonistic action at all.

PAF and Tx$A_2$ interact and contribute to asthma, arthritis, rhinitis, bronchitis, and rashes and other various allergenic, inflammatory, and hypersecretion type diseases and thrombosis of the circulatory system, pulmonary hypertension, and stomach ulcers, psoriasis, and other diseases. Accordingly, in the treatment of these diseases, a greater therapeutic effect can be expected by suppressing PAF and Tx$A_2$ simultaneously rather than suppressing PAF or Tx$A_2$ alone.

On the other hand, at the present time, a problem has arisen with "acquired resistance" in the chemotherapy of cancer wherein the effectiveness of the anti-cancer drug is lost during the treatment. Drug resistance to a variety of types of anti-cancer drugs is becoming a serious problem. As a method for overcoming this multi-drug resistance, it has been reported that concomitant administration of an anti-cancer drug and some calcium antagonists (nicardipine and other 1,4-dihydropyridine compounds etc.) is effective [Cancer Res., 41, 1967–1972 (1981), Cancer and Chemotherapy, vol. 11, pp. 750–759 (1984)].

Further, Japanese Unexamined Patent Publication (Kokai) No. 2-40383, Japanese Unexamined Patent Publication (Kokai) No. 2-240081, Japanese Examined Patent Publication (Kokoku) No. 6-92391 and Japanese Examined Patent Publication (Kokoku) No. 6-92401 describe compounds with dioxene rings or dithiene rings bonded at the 4-position of 1,4-dihydropyridine, while Japanese Unexamined Patent Publication (Kokai) No. 5-117235 and Japanese Unexamined Patent Publication (Kokai) No. 2-138221 describe compounds with a phenyl group or other aromatic ring bonded at the 4-position of the 1,4-dihydropyridine as having an action for overcoming resistance to anti-cancer drugs.

However, the inventions described in the above-mentioned Cancer Res., 41, 1967–1972 (1981), Cancer and Chemotherapy, vol. 11, pp. 750–759 (1984) use a drug having a calcium channel blocking action as a drug for overcoming resistance to anti-cancer drugs and has the defect that it is not necessarily practical from the viewpoint of the side-effects. That is, a calcium channel blocker is inherently powerful in action and in even very small amounts acts on the heart, arteries, etc., and therefore, has the defect that if a large amount of such a drug is used, will unavoidably have undesirable effects on the heart, arteries, etc.

Further, among the 1,4-dihydropyridines described in the above-mentioned publications, as described in Japanese Unexamined Patent Publication (Kokai) No. 2-40383 and Japanese Unexamined Patent Publication (Kokai) No. 2-240081, there are compounds which have an action reinforcing the effect of anti-cancer drugs or an action for overcoming resistance to anti-cancer drugs and further have almost no calcium channel blocking action, and therefore, are considerably preferable, but these compounds are not sufficiently satisfactory in terms of the effect of the action for overcoming resistance to anti-cancer drugs. Further, the 1,4-dihydropyridine compounds described in these publications all have as 4-position substituents a dioxene ring, dithiene ring, or other heterocyclic group or phenyl group or other aromatic ring group and do not include anything about a compound having an alkyl group, alkenyl group, cycloalkyl group etc.

DISCLOSURE OF INVENTION

Accordingly, the object of the present invention is to provide novel 1,4-dihydropyridine compounds having various substituents.

The other object of the present invention is to provide a compound having a superior PAF antagonistic action and thromboxane synthesis inhibiting action and further having an action causing a remarkable increase in the sensitivity of cancer cells to anti-cancer drugs, particularly the sensitivity of cancer cells acquiring resistance to anti-cancer drugs (action for overcoming resistance to anti-cancer drugs), exhibits an effect of prolonging the survival time of cancerous animals through concomitant use with an anti-cancer drug, and further has almost no calcium channel blocking action and is low in toxicity.

In accordance with the present invention, there is provided a 1,4-dihydropyridine compound having the formula (I):

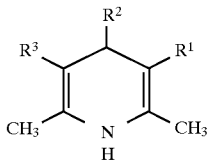

wherein, $R^1$ indicates —COO—A—(3-pyridyl), A indicates a $C_3$–$C_6$ straight chain alkylene group in which one piperazine may be interposed; $R^2$ indicates a $C_2$–$C_{10}$ alkyl group, alkenyl group or alkynyl group; a lower alkyl group or lower alkenyl group having a substituent; or a cycloalkyl group which may have a substituent; $R^3$ indicates the same group as $R^1$ or —COO—$R^4$; and $R^4$ indicates a lower alkyl group which may have a substituent or its pharmacologically acceptable salt.

In accordance with the present invention, there is also provided an anti-allergenic, antiphlogistic, a drug for overcoming resistance to anti-cancer drugs, or a drug for reinforcing the effect of anti-cancer drugs comprising a 1,4-dihydropyridine compound having formula (I) or its pharmacologically acceptable salt as effective ingredients

BEST MODE FOR CARRYING OUT THE INVENTION

The present invention will now be explained in further detail.

As preferable groups of $R^1$, a group where A is a trimethylene group, tetramethylene group or a $C_3$–$C_4$ straight chain alkylene group having a piperazine therein, especially, a trimethylene group may be exemplified.

As preferable groups of $R^3$, the same groups as $R^1$ may be exemplified. Further, $R^3$ may indicate —COO—$R^4$ where $R^4$ is a lower, (preferably $C_1$–$C_4$) alkyl group which may have a cyano, (substituted) amino group, phenyl or heterocyclic group having a nitrogen atom, in particular a lower alkyl group which may be substituted with a cyano, N-methyl-N-benzylamino, phenyl, phenylthio, pyridyl, pyridyloxy, substituted piperazino group, indolyl group, aziridinyl, tetrahydropyridyl, etc. may be exemplified.

As preferable groups of $R^2$, a $C_3$–$C_9$ alkyl group, alkenyl group or alkynyl group; a phenyl, furyl group or cycloalkyl group etc. substituted lower (preferably $C_1$–$C_4$) alkyl group or lower (preferably $C_1$–$C_4$) alkyl group; or cycloalkyl, which may have a substituent group such as lower (preferably $C_1$–$C_3$) alkynyl group such as methyl group or ethoxycarbonyl group, in particular, $C_3$–$C_8$ alkyl group may be exemplified. More specifically, an n-propyl, isopropyl, n-pentyl, n-octyl, 1-methylpropyl, 1-methylbutyl, 1-ethylpropyl, 1-ethylpentyl, 2,2-dimethylpropyl, 2,4,4-trimethylpentyl, benzyl, 1-phenylbenzyl, 1-phenylethyl, 2-phenylethyl, 3,3-dimethylcyclohexylmethyl, 2-methyl-1-propenyl, 2-furylethenyl, 2,6-dimethyl-5-heptenyl, 1-heptynyl, or cyclohexyl, cyclopentyl, ethoxycarbonylcyclopropyl, etc. may be exemplified. Particularly preferably, an isopropyl, n-propyl, n-pentyl, n-octyl, 1-methylpropyl, 1-methylbutyl, 1-ethylpropyl, 1-ethylpentyl, 2,2-dimethylpropyl, 2,4,4-trimethylpentyl, 2-methyl-1-propenyl, or 2,6-dimethyl-5-heptenyl, or cyclohexyl may be exemplified.

Specific examples of the preferred compounds are as follows.

(Compound 1) 2,6-dimethyl-4-isopropyl-1,4-dihydropyridine-3,5-dicarboxylic acid bis[3-(3-pyridyl)propyl]ester (Compound 2) 2,6-dimethyl-4-n-propyl-1,4-dihydropyridine-3,5-dicarboxylic acid bis[3-(3-pyridyl)propyl]ester (Compound 3) 2,6-dimethyl-4-(1-methylbutyl)-1,4-dihydropyridine-3,5-dicarboxylic acid bis[3-(3-pyridyl)propyl]ester (Compound 4) 2,6-dimethyl-4-(2,2-dimethylpropyl)-1,4-dihydropyridine-3,5-dicarboxylic acid bis[3-(3-pyridyl)propyl]ester (Compound 8) 2,6-dimethyl-4-cyclohexyl-1,4-dihydropyridine-3,5-dicarboxylic acid bis[3-(3-pyridyl)propyl]ester (Compound 11) 2,6-dimethyl-4-(2,6-dimethyl-5-heptenyl)-1,4-dihydropyridine-3,5-dicarboxylic acid bis [3-(3-pyridyl)propyl]ester (Compound 13) 2,6-dimethyl-4-isopropyl-1,4-dihydropyridine-3,5-dicarboxylic acid 3-methylester, 5-[3-(3-pyridyl)propyl]ester (Compound 15) 2,6-dimethyl-4-isopropyl-1,4-dihydropyridine-3,5-dicarboxylic acid 3-(4-pyridylmethyl)ester, 5-[3-(3-pyridyl)propyl]ester (Compound 16) 2,6-dimethyl-4-n-octyl-1,4-dihydropyridine-3,5-dicarboxylic acid bis[3-(3-pyridyl)propyl]ester (Compound 17) 2,6-dimethyl-4-(2-methyl-1-propenyl)-1,4-dihydropyridine-3,5-dicarboxylic acid bis[3-(3-pyridyl)propyl]ester (Compound 18) 2,6-dimethyl-4-n-pentyl-1,4-dihydropyridine-3,5-dicarboxylic acid bis[3-(3-pyridyl)propyl]ester (Compound 19) 2,6-dimethyl-4-(1-methylpropyl)-1,4-dihydropyridine-3,5-dicarboxylic acid bis[3-(3-pyridyl)propyl]ester (Compound 20) 2,6-dimethyl-4-(1-ethylpropyl)-1,4-dihydropyridine-3,5-dicarboxylic acid bis[3-(3-pyridyl)propyl]ester (Compound 21) 2,6-dimethyl-4-(1-ethylpentyl)-1,4-dihydropyridine-3,5-dicarboxylic acid bis[3-(3-pyridyl)propyl]ester (Compound 22) 2,6-dimethyl-4-(2,4,4-trimethylpentyl)-1,4-dihydropyridine-3,5-dicarboxylic acid bis[3-(3-pyridyl)propyl]ester (Compound 23) 2,6-dimethyl-4-n-octyl-1,4-dihydropyridine-3,5-dicarboxylic acid bis[2-(4-(3-pyridylmethyl)piperazin-1-yl)ethyl]ester (Compound 28) 2,6-dimethyl-4-isopropyl-1,4-dihydropyridine-3,5-dicarboxylic acid 3-[2-(4-(3-pyridylmethyl)piperazin-1-yl)ethyl]ester, 5-[3-(3-pyridyl)propyl]ester (Compound 30) 2,6-dimethyl-4-isopropyl-1,4-dihydropyridine-3,5-dicarboxylic acid bis[4-(3-pyridyl)butyl]ester (Compound 32) 2,6-dimethyl-4-(1-heptynyl)-1,4-dihydropyridine-3,5-dicarboxylic acid bis[3-(3-pyridyl)propyl]ester (Compound 33) 2,6-dimethyl-4-(3,3-dimethylcyclohexylmethyl)-1,4-dihydropyridine-3,5-dicarboxylic acid bis[3-(3-pyridyl)propyl]ester (Compound 34) 2,6-dimethyl-4-n-pentyl-1,4-dihydropyridine-3,5-dicarboxylic acid 3-[2-(N-benzyl-N-methylamino)ethyl]ester, 5-[3-(3-pyridyl)propyl]ester (Compound 40) 2,6-dimethyl-4-n-heptyl-1,4-dihydropyridine-3,5-dicarboxylic acid bis[3-(3-pyridyl)propyl]ester (Compound 41) 2,6-dimethyl-4-n-hexyl-1,4-dihydropyridine-3,5-dicarboxylic acid bis[3-(3-pyridyl)propyl]ester (Compound 42) 2,6-dimethyl-4-n-butyl-1,4-dihydropyridine-3,5-dicarboxylic acid bis[3-(3-pyridyl)propyl]ester (Compound 43) 2,6-dimethyl-4-(2-methylpropyl)-1,4-dihydropyridine-3,5-dicarboxylic acid bis[3-(3-pyridyl)propyl]ester The 1,4-dihydropyridine compounds having formula (I) provided by the present invention may all be produced according to known processes used for the production of 1,4-dihydropyridine compounds in the past.

That is, the compounds having formula (I) may be produced by the method of reacting the aldehydes having the formula (II) and the acetoacetic acid esters having the formula (III) and the 3-aminocrotonic acid esters having the formula (IV) in the presence or absence of an organic solvent (method A) or reacting the aldehydes having the formula (II) and the acetoacetic acid esters having the formula (III) in the presence of ammonia solution in an organic solvent (method B).

(Method A)

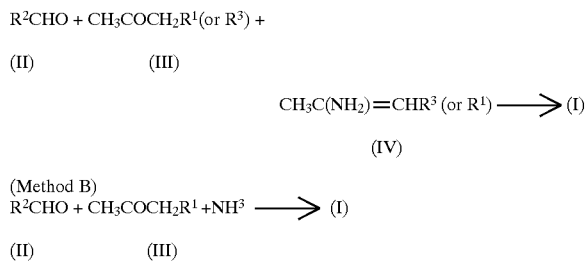

(Method B)
$R^2CHO + CH_3COCH_2R^1 + NH_3 \longrightarrow$ (I)

(II)            (III)

wherein, $R^1$, $R^2$ and $R^3$ are the same as defined in formula (I).

The reactions used in their production processes are basically the same as those of the known processes used for the production of 1,4-dihydropyridine compounds in the past (for example, the processes described in Japanese Examined Patent Publication (Kokoku) No. 46-40625 and No. 56-37225, Japanese Unexamined Patent Publication (Kokai) No. 60-214786, etc.) Accordingly, the 1,4-dihydropyridine compounds according to the present invention may be produced by suitable application of other reactions described in these publications in addition to the above-mentioned methods. The starting compounds used for these processes of production are all known compounds which may be easily obtained or produced by persons skilled in the art, if necessary. For example, acetoacetic acid esters may be produced by reacting diketene and alcohols. Further, 3-aminocrotonic acid esters may be produced by reacting ammonia gas with acetoacetic acid esters. The aldehydes may be easily produced by reduction of esters or oxidation of alcohols—which are known methods widely used for their synthesis. The compounds of formula (I) obtained by the present process may be separated and refined by known processing means (for example, extraction, chromatography, recrystallization, etc.)

The compounds according to the present invention or their pharmacologically acceptable salts have a platelet activating factor (PAF) antagonistic action and thromboxane $A_2$ (TxA$_2$) synthesis inhibiting action, and therefore, are useful as drugs for the treatment of inflammation and allergies. Further, the compounds according to the present invention or their pharmacologically acceptable salts exhibit an action for reinforcing the effect of anti-cancer drugs and further exhibit an action for overcoming resistance to anti-cancer drugs with respect to doxorubicin (adriamycin) resistant cancers and vincristine resistant cancers and prolong the survival time of cancerous animals by concomitant use with anti-cancer drugs. Thus, they are useful as drugs for overcoming resistance to anti-cancer drugs or drugs for reinforcing the effect of anti-cancer drugs.

When the compounds according to the present invention are used as antiphlogistics and anti-allergenics or as drugs for overcoming the resistance to anti-cancer drugs or drugs for reinforcing the effect of anti-cancer drugs, they may be administered by a suitable oral or non-oral method of administration. As a form of oral administration, tablets, granules, capsules, pills, dispersions, liquids, etc., may be exemplified. Further as a form of non-oral administration, injections, suppositories, etc. may be exemplified. These preparations may be prepared in accordance with ordinary methods using the compounds of the present invention or their pharmacologically acceptable salts and ordinary pharmacologically acceptable carriers.

For example, in the case of oral administration, the preparations can be prepared into the desired form using excipients such as lactose, glucose, corn starch, sucrose, and disintegrators such as calcium carboxymethylcellulose, hydroxypropylcellulose, and lubricants such as, calcium stearate, magnesium stearate, talc, polyethylene glycol, hydrogenated oil, and binders such as hydroxypropylcellulose, hydroxypropylmethylcellulose, carboxymethylcellulose, polyvinyl alcohol, gelatin, arabia gum, and humectants such as glycerine, ethylene glycol, and in addition when necessary, surfactants, taste adjusters, etc.

Further, in the case of a non-oral drug, diluents such as water, ethanol, glycerine, propylene glycol, polyethylene glycol, agar, tragacanth gum may be used and, if necessary, solution adjuvants, buffer agents, preservatives, flavors, coloring agents, etc. may be used.

When formulating the compounds according to the present invention as anti-allergenics or antiphlogistics, the dosage, as the compounds according to the present invention, is, per adult, in the case of oral administration, 1 to 300 mg per day, preferably 1 to 100 mg, and in the case of non-oral administration, 0.1 to 100 mg per day, preferably 0.5 to 30 mg. The desired effect of treatment can be expected by administration divided into 1 to 3 dosages per day.

When formulating the compounds according to the present invention as drugs for overcoming resistance to anti-cancer drugs or drugs for reinforcing the effect of anti-cancer drugs, the unit dosage as the compound according to the present invention is, per adult, in the case of oral administration, 5 to 1000 mg per day, preferably 5 to 200 mg, and in the case of non-oral administration, 1 to 500 mg per day, preferably 1 to 200 mg. The desired effect of treatment can be expected by administration divided into 1 to 3 dosages per day.

EXAMPLES

The Synthesis Examples, a Preparation Example, and Test Examples of the compound according to the present invention will be illustrated as examples below:

Synthesis Examples

Synthesis examples will be shown below. The NMR data, however, shows the signals or main signals of $^1$H-NMR measured by a CDCl$_3$ solvent.

Example 1

Synthesis of 2,6-dimethyl-4-isopropyl-1,4-dihydropyridine-3,5-dicarboxylic acid bis[3-(3-pyridyl)propyl]ester (Compound 1)

2.2 g of acetoacetic acid 3-(3-pyridyl)propyl ester, 2.2 g of 3 aminocrotonic acid 3-(3-pyridyl)propyl ester, and 0.9 g of isobutylaldehyde were heated and refluxed in 10 ml of isopropanol for 7 hours. After the reaction, the reaction solution was condensed to dryness under reduced pressure, The residue was dissolved in 1N hydrochloric acid, washed by ethyl acetate, then made alkaline by sodium hydroxide and extracted by ethyl acetate. The extracted solution was rinsed, then dried over anhydrous sodium sulfate and condensed to dryness under reduced pressure, then the oily substance was refined by silica gel column chromatography to obtain the target compound in an amount of 3.0 g (63.0%).

NMR:0.78 (6 H,d), 1.62 (1 H,m), 1.98 (4 H,m), 2.32 (6 H,s), 2.72 (4 H,t), 3.99 (1 H,d), 4.14 (4 H,m), 6.00 (1 H,br), 7.17 (2 H,m), 7.47 (2 H,m), 8.42–8.43 (4 H,m)

Example 2

Synthesis of 2,6-dimethyl-4-n-propyl-1,4-dihydropyridine-3,5-dicarboxylic acid bis[3-(3-pyridyl)propyl]ester (Compound 2)

2.2 g of acetoacetic acid 3-(3-pyridyl)propyl ester and 0.36 g of n-butylaldehyde were heated and refluxed in the presence of 1 ml of concentrated ammonia solution in 20 ml of isopropanol for 7 hours. After the reaction, the reaction solution was condensed to dryness under reduced pressure, the residue was dissolved in 1N hydrochloric acid, washed with ethyl acetate, then made alkaline by sodium hydroxide and extracted by ethyl acetate. The extracted solution was rinsed, then dried over anhydrous sodium sulfate and condensed to dryness under reduced pressure, then the oily substance was refined by silica gel column chromatography to obtain the target compound in an amount of 1.24 g (51.9%).

NMR:0.86 (3 H,t), 1.33 (2 H,m), 1.34 (2 H,m), 1.99 (4 H,m), 2.30 (6 H,s), 2.72 (4 H,t), 4.00 (1 H,t), 4.15 (4 H,m), 5.88 (1 H,br), 7.18 (2 H,m), 7.47 (2 H,m), 8.42–8.44 (4 H,m)

The compounds of the examples obtained by synthesis according to Example 1 and Example 2 will be given below along with the materials used and the NMR analysis values. Further, the compounds were refined by recrystallizing the obtained crude substances by a suitable solvent or when necessary by applying silica gel column chromatography.

Example 3

2,6-dimethyl-4-(1-methylbutyl)-1,4-dihydropyridine-3,5-dicarboxylic acid bis[3-(3-pyridyl) propyl]ester (Compound 3)

Materials:

Acetoacetic acid 3-(3-pyridyl)propyl ester 3-aminocrotonic acid 3-(3-pyridyl)propyl ester 2-methyl-n-valerylaldehyde NMR:0.75 (3 H,d), 0.82 (3 H,t), 0.98–1.46 (5 H,m), 2.00 (4 H,m), 2.31 (3 H,s), 2.32 (3 H,s), 2.73 (4 H,m), 4.07 (1 H,d), 4.15 (4 H,m), 5.65 (1 H,br), 7.18 (2 H,m), 7.47 (2 H,m), 8.43–8.44 (4 H,m)

Example 4

2,6-dimethyl-4-(2,2-dimethylpropyl)-1,4-dihydropyridine-3,5-dicarboxylic acid bis[3-(3-pyridyl)propyl]ester (Compound 4)

Materials:

Acetoacetic acid 3-(3-pyridyl)propyl ester 3-aminocrotonic acid 3-(3-pyridyl)propyl ester 3,3-dimethylbutylaldehyde NMR:0.91 (9 H,s), 1.22 (2 H,d), 2.01 (4 H,m), 2.33 (6 H,s), 2.73 (4 H,t), 4.12–4.20 (5 H,m), 5.95 (1 H,br), 7.18 (2 H,m), 7.47 (2 H,m), 8.43–8.44 (4 H,m)

Example 5

2,6-dimethyl-4-benzyl-1,4-dihydropyridine-3,5-dicarboxylic acid bis[3-(3-pyridyl)propyl]ester (Compound 5)

Materials:

Acetoacetic acid 3-(3-pyridyl)propyl ester Aminocrotonic acid 3-(3-pyridyl)propyl ester Phenylacetoaldehyde NMR:1.91 (4 H,m), 2.22 (6 H,s), 2.62 (2 H,d), 2.69 (4 H,t), 3.96–4.09 (4 H,m), 4.26 (1 H,t), 5.92 (1 H,br), 7.03–7.21 (7 H,m), 7.48 (2 H,m), 8.42–8.44 (4 H,m)

Example 6

2,6-dimethyl-4-benzhydryl-1,4-dihydropyridine-3,5-dicarboxylic acid bis[3-(3-pyridyl)propyl]ester (Compound 6)

Materials:

Acetoacetic acid 3-(3-pyridyl)propyl ester Aminocrotonic acid 3-(3-pyridyl)propyl ester Diphenylacetoaldehyde NMR:1.84 (4 H,m), 2.24 (6 H,s), 2.62 (4 H,t), 3.71 (4 H,m), 3.94 (1 H,m), 4.94 (1 H,d), 6.00 (1 H,br), 7.09–7.32 (12 H,m), 7.45 (2 H,m), 8.43–8.45 (4 H,m)

Example 7

2,6-dimethyl-4-(1-phenylethyl)-1,4-dihydropyridine-3,5-dicarboxylic acid bis[3-(3-pyridyl)propyl]ester (Compound 7)

Materials:

Acetoacetic acid 3-(3-pyridyl)propyl ester Aminocrotonic acid 3-(3-pyridyl)propyl ester 2-phenylpropionaldehyde NMR:1.19 (3 H,d), 1.82–1.96 (5 H,m), 2.22 (6 H,d), 2.68 (4 H,m), 4.02 (4 H,m), 4.33 (1 H,d), 5.63 (1 H,br), 7.10 (2 H,m), 7.15–7.26 (5 H,m), 7,46 (2 H,m), 8.43–8.44 (4 H,m)

Example 8

2,6-dimethyl-4-cyclohexyl-1,4-dihydropyridine-3,5-dicarboxylic acid bis[3-(3-pyridyl)propyl]ester (Compound 8)

Materials:

Acetoacetic acid 3-(3-pyridyl)propyl ester Aminocrotonic acid 3-(3-pyridyl)propyl ester Cyclohexylaldehyde NMR:0.91–1.7 (11 H,m), 1.99 (4 H,m), 2.32 (6 H,s), 2.73 (4 H,t), 3.99 (1 H,d), 4.14 (4 H,m), 5.84 (1 H,br), 7.18 (2 H,m), 7.47 (2 H,m), 8.42–8.44 (4 H,m)

Example 9

2,6-dimethyl-4-(2-ethoxycarbonylcyclopropyl)-1,4-dihydropyridine-3,5-dicarboxylic acid bis[3-(3-pyridyl)propyl]ester (Compound 9)

Materials:

Acetoacetic acid 3-(3-pyridyl)propyl ester 3-aminocrotonic acid 3-(3-pyridyl)propyl ester Ethyl 2-formylcyclopropancarboxylate NMR:0.88–1.64 (9 H,m), 2.03 (4 H,m), 2.32 (3 H,s), 2.33 (3 H,s), 2.71 (4 H,m), 3.82 (1 H,d), 4.00–4.21 (4 H,m), 6.04 (1 H,br), 7.19 (2 H,m), 7.49 (2 H,m), 8.43–8.46 (4 H,m)

Example 10

2,6-dimethyl-4-(2-(2-furyl) ethenyl)-1,4-dihydropyridine-3,5-dicarboxylic acid bis[3-(3-pyridyl)propyl]ester (Compound 10)

Materials:

Acetoacetic acid 3-(3-pyridyl)propyl ester 3-aminocrotonic acid 3-(pyridyl)propylester 3-(2-furyl)acrolein NMR:1.99 (4 H,m), 2.34 (6 H,s), 2.71 (4 H,t), 4.10–4.24 (4 H,m), 4.65 (1 H,d), 5.95 (1 H,br), 6.11–6.31 (5 H,m), 7.14 (2 H,m), 7.42 (2 H,m), 8.41–8.43 (4 H,m)

Example 11

2,6-dimethyl-4-(2,6-dimethyl-5-heptenyl)-1,4-dihydropyridine-3,5-dicarboxylic acid bis[3-(3-pyridyl)propyl]ester (Compound 11)

Materials:

Acetoacetic acid 3-(3-pyridyl)propyl ester 3-aminocrotonic acid 3-(3-pyridyl)propyl ester Citronellal NMR:0.93 (3 H,d), 1.12–1.36 (7 H,m), 1.55 (3 H,s), 1.62 (3 H,s), 1.99 (4 H,m), 2.31 (6 H,s), 2.72 (4 H,m), 4.05 (1 H,m), 4.15 (4 H,t), 5.02 (1 H,m), 5.94 (1 H,br), 7.17 (2 H,m), 7.47 (2 H,m), 8.42–8.44 (4 H,m)

Example 12

2,6-dimethyl-4-(2-phenylethyl)-1,4-dihydropyridine-3,5-dicarboxylic acid bis[3-(3-pyridyl)propyl]ester (Compound 12)

Materials:

Acetoacetic acid 3-(3-pyridyl)propyl ester 3-aminocrotonic acid 3-(3-pyridyl)propyl ester Hydrocinnamaldehyde NMR:1.71 (2 H,m), 1.98 (4 H,m), 2.32 (6 H,s), 2.57 (2 H,m), 2.71 (4 H,t), 4.13–4.18 (5 H,m), 6.06 (1 H,br), 7.11–7.20 (7 H,m), 7.45 (2 H,m), 8.42–8.43 (4 H,m)

Example 13

2,6-dimethyl-4-isopropyl-1,4-dihydropyridine-3,5-dicarboxylic acid 3-methylester 5-[3-(3-pyridyl)propyl]ester (Compound 13)

Materials:

Acetoacetic acid 3-(3-pyridyl)propyl ester 3-aminocrotonic acid methylester

Isobutylaldehyde

NMR:0.74 (6 H,m), 1.58 (1 H,m), 1.99 (2 H,m), 2.30 (6 H,d), 2.73 (2 H,t), 3.70 (3 H,s), 3.92 (1 H,d), 4.13 (2 H,m), 6.08 (1 H,br), 7.21 (1 H,m), 7.51 (1 H,m), 8.42–8.46 (2 H,m)

Example 14

2,6-dimethyl-4-n-octyl-1,4-dihydropyridine-3,5-dicarboxylic acid 3-(2-cyanoethyl) ester, 5-[3-(3-pyridyl)propyl]ester (Compound 14)

Materials:

Acetoacetic acid 2-cyanoethylester 3-aminocrotonic acid 3-(3-pyridyl)propyl ester Nonylaldehyde NMR:0.85 (3 H,m), 1.21–1.34 (14 H,m), 2.02 (2 H,m), 2.31 (3 H,s), 2.32 (3 H,s), 2.69–2.77 (4 H,m), 3.96 (1 H,t), 4.14 (2 H,m), 4.35 (2 H,m), 5.80 (1 H,br), 7.22 (1 H,m), 7.53 (1 H,m), 8.44–8.47 (2 H,m)

Example 15

2,6-dimethyl-4-isopropyl-1,4-dihydropyridine-3,5-dicarboxylic acid 3-(4-pyridylmethyl) ester, 5-[3-(3-pyridyl)propyl]ester (Compound 15)

Materials:

Acetoacetic acid 4-pyridylmethylester 3-aminocrotonic acid 3-(3-pyridyl)propyl ester Isobutylaldehyde NMR:0.77 (6 H,m), 1.64 (1 H,m), 2.01 (2 H,m), 2.33 (6 H,d), 2.73 (2 H,m), 4.04 (1 H,d), 4.17 (2 H,m), 5.19 (2 H,m), 6.39 (1 H,br), 7.20 (1 H,m), 7.28 (2 H,m), 7.48 (1 H,m), 8.43–8.45 (2 H,m), 8.55 (2 H,m)

Example 16

2,6-dimethyl-4-n-octyl-1,4-dihydropyridine-3,5-dicarboxylic acid bis[3-(3-pyridyl)propyl]ester (Compound 16)

Materials:

Acetoacetic acid 3-(3-pyridyl)propyl ester 3-aminocrotonic acid 3-(3-pyridyl)propyl ester Nonylaldehyde NMR:0.84 (3 H,t), 1.20–1.35 (14 H,m), 2.00 (4 H,m), 2.31 (6 H,s), 2.73 (4 H,t), 4.00 (1 H,t), 4.16 (4 H,m), 5.77 (1 H,br), 7.19 (2 H,m), 7.48 (2 H,m), 8.43–8.45 (4 H,m)

Example 17

2,6-dimethyl-4-(2-methyl-1-propenyl)-1,4-dihydropyridine-3,5-dicarboxylic acid bis[3-(3-pyridyl)propyl]ester (Compound 17)

Materials:

Acetoacetic acid 3-(3-pyridyl)propyl ester 3-methyl-2-butenal

Ammonia solution

NMR:1.62 (3 H,d), 1.81 (3 H,d), 1.99 (4 H,m), 2.30 (6 H,s), 2.71 (4 H,t), 4.15 (4 H,m), 4.64 (1 H,d), 4.99 (1 H,d), 5.70 (1 H,br), 7.19 (2 H,m), 7.48 (2 H,m), 8.43–8.45 (4 H,m)

Example 18

2,6-dimethyl-4-n-pentyl-1,4-dihydropyridine-3,5-dicarboxylic acid bis[3-(3-pyridyl)propyl]ester (Compound 18)

Materials:

Acetoacetic acid 3-(3-pyridyl)propyl ester

Capronaldehyde

Ammonia solution

NMR:0.83 (3 H,t), 1.23–1.36 (8H,m), 2.00 (4 H,m), 2.31 (6 H,s), 2.74 (4 H,t), 4.01 (1 H,t), 4.16 (4 H,m), 6.52 (1 H,br), 7.19 (2 H,m), 7.49 (2 H,m), 8.43–8.45 (4 H,m)

Example 19

2,6-dimethyl-4-(1-methylpropyl)-1,4-dihydropyridine-3,5-dicarboxylic acid bis[3-(3-pyridyl)propyl]ester (Compound 19)

Materials:

Acetoacetic acid 3-(3-pyridyl)propyl ester 3-aminocrotonic acid 3-(3-pyridyl)propyl ester 2-methylbutylaldehyde NMR:0.76 (3 H,d), 0.86 (3 H,t), 1.00 (1 H,m), 1.37 (2 H,m), 2.00 (4 H,m), 2.32 (6 H,d), 2.72 (4 H,m), 4.07 (1 H,d), 4.15 (4 H,m), 5.70 (1 H,br), 7.18 (2 H,m), 7.48 (2 H,m), 8.43–8.44 (4 H,m)

Example 20

2,6-dimethyl-4-(1-ethylpropyl)-1,4-dihydropyridine-3,5-dicarboxylic acid bis[3-(3-pyridyl)propyl]ester (Compound 20)

Materials:

Acetoacetic acid 3-(3-pyridyl)propyl ester 3-aminocrotonic acid 3-(3-pyridyl)propyl ester 2-ethyl-n-butylaldehyde NMR:0.88 (6 H,t), 1.09–1.22 (5 H,m), 2.00 (4 H,m), 2.31 (6 H,s), 2.73 (4 H,t), 4.10–4.19 (5 H,m), 5.72 (1 H,br), 7.18 (2 H,m), 7.48 (2 H,m), 8.43–8.44 (4 H,m)

Example 21

2,6-dimethyl-4-(1-ethylpentyl)-1,4-dihydropyridine-3,5-dicarboxylic acid bis[3-(3-pyridyl)propyl]ester (Compound 21)

Materials:

Acetoacetic acid 3-(3-pyridyl)propyl ester 3-aminocrotonic acid 3-(3-pyridyl)propyl ester 2-ethylhexylaldehyde NMR:0.84 (3 H,t), 0.88 (3 H,t), 1.17–1.23 (9 H,m), 2.00 (4 H,m), 2.31 (6 H,d), 2.72 (41 H,t), 4.10–4.18 (5 H,m), 5.83 (1 H,br), 7.18 (2 H,m), 7.48 (2 H,m), 8.43–8.44 (4 H,m)

Example 22

2,6-dimethyl-4-(2,4,4-trimethylpentyl)-1,4-dihydropyridine-3,5-dicarboxylic acid bis[3-(3-pyridyl)propyl]ester (Compound 22)

Materials:

Acetoacetic acid 3-(3-pyridyl)propyl ester 3-aminocrotonic acid 3-(3-pyridyl)propyl ester 3,5,5-trimethylhexanal NMR:0.80 (9 H,s), 1.00–1.44 (8 H,m), 2.01 (4 H,m), 2.31 (3 H,s), 2.32 (3 H,s), 2.73 (4 H,m), 4.01 (1 H,m), 4.17 (4 H,m), 5.80 (1 H,br), 7.19 (2 H.m), 7.48 (2 H,m), 8.45 (4 H,m)

Example 23

2,6-dimethyl-4-n-octyl-1,4-dihydropyridine-3,5-dicarboxylic acid bis[2-(4-(3-pyridylmethyl)piperazin-1-yl)ethyl]ester (Compound 23)

Materials:

Acetoacetic acid 2-(4-(3-pyridylmethyl)piperazin-1-yl)ethyl ester

Nonylaldehyde

Ammonia solution

NMR:0.86 (3 H,t), 1.17–1.28 (14 H,m), 2.28 (6 H,s), 2.48–2.57 (16 H,m), 2.67 (4 H,t), 3.51 (4 H,s), 3.89 (1 H,t), 4.16–4.31 (4 H,m), 5.89 (1 H,br), 7.25 (2 H,m), 7.66 (2 H,m), 8.49–8.53 (4 H,m)

Example 24

2,6-dimethyl-4-isopropyl-1,4-dihydropyridine-3,5-dicarboxylic acid 3-[3-(2-chlorophenyl)propyl]ester, 5-[3-(3-pyridyl) propyl]ester (Compound 24)

Materials:

Acetoacetic acid 3-(2-chlorophenyl)propyl ester 3-aminocrotonic acid 3-(3-pyridyl)propyl ester Isobutylaldehyde NMR:0.74 (6 H,dd), 2.31 (3 H,s), 2.35 (3 H,s), 2.58 (2 H,t), 2.60 (2 H,t), 4.03 (1 H,d), 7.1–8.5 (8 H,m)

Example 25

2,6-dimethyl-4-isopropyl-1,4-dihydropyridine-3,5-dicarboxylic acid 3-(2-phenylthioethyl) ester, 5-[3-(3-pyridyl)propyl]ester (Compound 25)

Materials:

Acetoacetic acid 2-( phenylthioethyl) ester 3-aminocrotonic acid 3-(3-pyridyl)propyl ester Isobutylaldehyde NMR:0.76 (6 H,dd), 2.26 (2 H,t), 2.30 (3 H,s), 2.34 (3 H,s), 3.96 (1 H,d), 4.0–4.1 (4 H,m), 6.1–8.5 (9 H,m)

Example 26

2,6-dimethyl-4-isopropyl-1,4-dihydropyridine-3,5-dicarboxylic acid 3-[3-(4-pyridyl)propyl]ester, 5-[3-(3-pyridyl)propyl]ester (Compound 26)

Materials:

Acetoacetic acid 3-(4-pyridyl)propyl ester 3-aminocrotonic acid 3-(3-pyridyl)propyl ester Isobutylaldehyde NMR:0.75 (6 H,dd), 2.34 (6 H,s), 2.56 (4 H,m), 3.88 (1 H,d), 7.0–8.6 (8 H,m)

Example 27

2,6-dimethyl-4-isopropyl-1,4-dihydropyridine-3,5-dicarboxylic acid 3-[3-(2-pyridyl) propyl]ester, 5-[3-(3-pyridyl)propyl]ester (Compound 27)

Materials:

Acetoacetic acid 3-(2-pyridyl)propyl ester 3-aminocrotonic acid 3-(3-pyridyl)propyl ester Isobutylaldehyde NMR:0.78 (6 H,dd), 2.34 (6 H,s), 2.71 (4 H,m), 3.85 (1 H,d), 7.0–8.6 (8 H,m)

Example 28

2,6-dimethyl-4-isopropyl-1,4-dihydropyridine-3,5-dicarboxylic acid 3-[2-(4-(3-pyridylmethyl)piperazin-1-yl)ethyl]ester, 5-[3-(3-pyridyl)propyl]ester (Compound 28)

Materials:

Acetoacetic acid 2-(4-(3-pyridylmethyl)piperazin-1-yl)ethyl ester 3-aminocrotonic acid 3-(3-pyridyl)propyl ester Isobutylaldehyde NMR: 0.79 (6 H,dd), 2.29 (6 H,s), 2.55 (2 H,t), 3.99 (1 H,d), 7.0–8.6 (8 H,m)

Example 29

2,6-dimethyl-4-isopropyl-1,4-dihydropyridine-3,5-dicarboxylic acid 3-n-butylester, 5-[3-(3-pyridyl)propyl] ester (Compound 29)

Materials:

Acetoacetic acid n-butylester 3-aminocrotonic acid 3-(3-pyridyl)propyl ester

Isobutylaldehyde

NMR:0.79 (6 H,d), 0.88 (3 H,t), 2.33 (3 H,s), 2.39 (3 H,s), 2.56 (2 H,t), 3.97 (1 H,d), 7.0–8.6 (4 H,m)

Example 30

2,6-dimethyl-4-isopropyl-1,4-dihydropyridine-3,5-dicarboxylic acid bis[4-(3-pyridyl)butyl]ester (Compound 30)

Materials:

Acetoacetic acid 4-(3-pyridylbutyl) ester

Isobutylaldehyde

Ammonia solution

NMR:0.73 (6 H,d), 2.30 (6 H,s), 2.63 (2 H,t), 3.91 (1 H,d), 6.7–8.3 (8 H,m)

Example 31

2,6-dimethyl-4-isopropyl-1,4-dihydropyridine-3,5-dicarboxylic acid 3-[2-(3-pyridyloxy) ethyl]ester, 5-[3-(3-pyridyl) propyl]ester (Compound 31)

Materials:

Acetoacetic acid 2-(3-pyridyloxy)ethyl ester 3-aminocrotonic acid 3-(3-pyridyl)propyl ester Isobutylaldehyde NMR:0.76 (6 H,dd), 2.30 (3 H,s), 2.32 (3 H,s), 2.69 (2 H,t), 3.98 (1 H,d), 4.2–4.6 (4 H,m), 7.1–8.4 (8 H,m)

Example 32

2,6-dimethyl-4-(1-heptynyl)-1,4-dihydropyridine-3,5-dicarboxylic acid bis[3-(3-pyridyl)propyl]ester (Compound 32)

Materials:

Acetoacetic acid 3-(3-pyridyl)propyl ester 3-aminocrotonic acid 3-(3-pyridyl)propyl ester 2-octynal NMR:0.79 (3 H,t), 1.15–1.39 (6 H,m), 1.98–2.08 (6 H,m), 2.33 (6 H,s), 2.78 (4 H,m), 4.11 (2 H,m), 4.26 (2 H,m), 4.81 (1 H,s), 5.94 (1 H,br), 7.18 (2 H,m), 7.51(2 H,m), 8.43–8.47 (4 H,m)

Example 33

2,6-dimethyl-4-(3,3-dimethylcyclohexylmethyl)-1,4-dihydropyridine-3,5-dicarboxylic acid bis[3-(3-pyridyl)propyl]ester (Compound 33)

Materials:

Acetoacetic acid 3-(3-pyridyl)propyl ester 3-aminocrotonic acid 3-(3-pyridyl)propyl ester (3,3-dimethylcyclohexyl)acetaldehyde NMR:0.69 (2 H,t), 0.80 (3 H,s), 0.83 (3 H,s), 1.01–1.83 (9 H,m), 2.01 (4 H,m), 2.31 (3 H,s), 2.32 (3 H,s), 2.73 (4 H,m), 4.08 (1 H,t), 4.16 (4 H,m), 6.06 (1 H,br), 7.19 (2 H,m), 7.48 (2 H,m), 8.43–8.45 (4 H,m)

Example 34

2,6-dimethyl-4-n-pentyl-1,4-dihydropyridine-3,5-dicarboxylic acid 3-[2-(N-benzyl-N-methylamino)ethyl] ester, 5-[3-(3-pyridyl)propyl]ester (Compound 34)

Materials:

Acetoacetic acid 3-(3-pyridyl)propyl ester 3-aminocrotonic acid 2-(N-benzyl-N-methylamino)ethyl ester Capronaldehyde NMR:0.82 (3 H,t), 1.19–1.33 (8 H,m), 1.97 (2 H,m), 2.25 (3 H,s), 2.29 (3 H,s), 2.30 (3 H,s), 2.68–2.74 (4 H,m), 3.55 (2 H,s), 3.98 (1 H,t), 4.06–4.19 (2 H,m), 4.27(2 H,m), 5.76 (1 H,br), 7.18–7.31 (6 H,m), 7.48 (1 H,m), 8.44–8.45 (2 H,m)

Example 35

2,6-dimethyl-4-n-pentyl-1,4-dihydropyridine-3,5-dicarboxylic acid 3-[3-(1-methyl-1,2,5,6-tetrahydro) pyridylmethyl]ester, 5-[3-(3-pyridyl) propyl]ester (Compound 35)

Materials:

Acetoacetic acid 3-(1-methyl-1,2,5,6-tetrahydro) pyridylmethylester 3-aminocrotonic acid 3-(3-pyridyl) propyl ester Capronaldehyde NMR:0.83 (3 H,t), 1.21–1.34 (8 H,m), 2.01 (2 H,m), 2.18 (2 H,m), 2.30 (6 H,d), 2.33 (3 H,s), 2.45 (2 H,t), 2.74 (2 H,m), 2.92 (2 H,br), 3.97 (2 H,t), 4.15 (2 H,m), 4.55 (2 H,br), 5.80 (1 H,br), 6.06 (1 H,br), 7.22 (1 H,m), 7.52 (1 H,m), 8.45–8.46 (2 H,m)

Example 36

2,6-dimethyl-4-n-pentyl-1,4-dihydropyridine-3,5-dicarboxylic acid 3-[2-(3-indolyl) ethyl]ester, 5-[3-(3-pyridyl)propyl]ester (Compound 36)

Materials:

Acetoacetic acid 2-(3-indolyl)ethyl ester 3-aminocrotonic acid 3-(3-pyridyl)propyl ester Capronaldehyde NMR:0.81 (3 H,t), 1.17–1.30 (8 H,m), 2.00 (2 H,m), 2.26 (3 H,s), 2.29 (3 H,s), 2.72 (2 H,t), 3.14 (2 H,t), 4.00 (1 H,t), 4.10 (1 H,m), 4.19 (1 H,m), 4.44 (2 H,m), 5.78 (1 H,br), 7.06–7.22 (4 H,m), 7.33 (1 H,d), 7.50 (1 H,m), 7.61 (1 H,d), 8.40 (1 H,br), 8.44–8.46 (2 H,m)

Example 37

2,6-dimethyl-4-n-pentyl-1,4-dihydropyridine-3,5-dicarboxylic acid 3-[2-(1-aziridinyl) ethyl]ester, 5-[3-(3-pyridyl)propyl]ester (Compound 37)

Materials:

Acetoacetic acid 2-(1-aziridinyl)ethyl ester 3-aminocrotonic acid 3-(3-pyridyl)propyl ester Capronaldehyde NMR:0.83 (3 H,t), 1.19–1.34 (10 H,m), 1.94 (1 H,m), 2.02 (2 H,m), 2.30 (3 H,s), 2.31 (3 H,s), 2.50 (2 H,m), 2.74 (2 H,t), 4.00 (1 H,t), 4.16 (2 H,m), 4.31 (2 H,m), 5.81 (1 H,br), 7.22 (1 H,m), 7.52 (1 H,m), 8.45–8.47 (2 H,m)

Example 38

2,6-dimethyl-4-n-pentyl-1,4-dihydropyridine-3,5-dicarboxylic acid 3-[3-(4-methylpiperazin-1-yl)propyl] ester, 5-[3-(3-pyridyl) propyl]ester (Compound 38)

Materials:

Acetoacetic acid 3-(4-methylpiperazin-1-yl)propyl ester 3-aminocrotonic acid 3-(3-pyridyl)propyl ester Capronaldehyde NMR:0.83 (3 H,t), 1.20–1.32 (8 H,m), 1.86 (2 H,m), 1.97–2.76 (23 H,m), 3.59 (1 H,t), 4.09–4.21 (4 H,m), 5.78 (1 H,br), 7.23 (1 H,m), 7.52 (1 H,m), 8.44–8.46 (2 H,m)

Example 39

2,6-dimethyl-4-n-pentyl-1,4-dihydropyridine-3,5-dicarboxylic acid 3-[2-(4-methyl-5-thiazolyl)ethyl]ester, 5-[3-(3-pyridyl) propyl]ester (Compound 39)

Materials:

Acetoacetic acid 3-(3-pyridyl)propyl ester 3-aminocrotonic acid 2-(4-methyl-5-thiazolyl)ethyl ester Capronaldehyde NMR:0.83 (3 H,t), 1.17–1.29 (8 H,m), 2.02 (2 H,m), 2.26 (3 H,s), 2.30 (3 H,s), 2.41 (3 H,s), 2.73 (2 H,t), 3.14 (2 H,t), 3.96 (1 H,t), 4.16 (2 H,m), 4.31 (2 H,m), 5.85 (1 H,br), 7.22 (1 H,m), 7.51 (1 H,m), 8.44–8.47 (2 H,m), 8.54 (1 H,s)

Preparation Examples

Example 40

(Preparation of Tablets)

| | |
|---|---|
| Compound of present invention (Compound 1) | 25 g |
| Lactose | 62 g |
| Corn starch | 40 g |
| Hydroxypropylcellulose | 2 g |
| Magnesium stearate | 1 g |

The above compound of the present invention, lactose and corn starch were mixed until becoming homogeneous, then a 5 W/V % solution of hydroxypropylcellulose was added and the mixture was mixed and granulated. The granules were graded by passing them through a 16 mesh sieve, then were formed into tablets by an ordinary method to form tablets of a weight per tablet of 130 mg, a diameter of 7 mm, and a content of the drug of 25 mg.

TEST EXAMPLES

Test Example 1
PAF Antagonistic Action Test

Japanese white rabbits (2.5 to 3.0 kg, Clean Experimental Animal Center) were used. Nine volumes of blood were taken with respect to one volume of 3.8% sodium citrate from the carotid artery under anesthesia by pentobarbitol. This was centrifuged at 1000 rpm and room temperature for 10 minutes. The top layer was used as the platelet rich plasma (PRP). The lower layer was further centrifuged at 3000 rpm and room temperature for 10 minutes to obtain the platelet poor plasma (PPP).

5 μl of the test compound was added to 90 μl of PRP. This was incubated at 37° C. for 3 minutes, then a platelet activating factor (PAF, final concentration 30 nM) was added to cause aggregation and the aggregation reaction was measured for 5 minutes using an aggrigometer (MC Medical, PAT-606).

The test results are shown in Table 1.

Test Example 2
$TxA_2$ Synthesis Inhibiting Action Test

One ml of a buffer (20 mM Tris-HCl buffer, 1 mM EDTA, pH 7.5) containing human blood platelet microsomes (50 μg protein/ml) and the test compound (final concentration $10^{-7}$M) was agitated, then incubated at 0° C. for 30 minutes. To this was added prostaglandin $H_2$ (100 ng/2 μl). This was incubated at 23° C. for 3 minutes to cause a reaction. Next, 1M hydrochloric acid was added to make the solution acidic and stop the reaction, then this was neutralized by 1M Tris-Base and centrifuged at 3000 rpm for 20 minutes. The amount of the $TxB_2$ in the supernatant was measured by the EIA method (Cayman Co. kit). The test results are shown in Table 1.

TABLE 1

| Compound no. | PAF antagonistic action Rate of suppression at $10^{-5}$ mol (%) | $TxA_2$ synthesis inhibiting action Rate of suppression at $10^{-7}$ mol (%) |
|---|---|---|
| Compound 1 | 82.7 | 90.7 |
| Compound 2 | 100 | 72.0 |
| Compound 3 | 88.8 | 82.4 |
| Compound 4 | 63.0 | 49.1 |
| Compound 8 | 31.2 | 63.0 |
| Compound 13 | 65.1 | 71.4 |
| Compound 15 | 70.2 | 83.5 |
| Compound 28 | 78.1 | 60.2 |
| Compound 30 | 67.1 | 69.7 |
| Control 1 | 16.2 | 74.7 |
| Control 2 | −2.0 | 77.9 |
| Control 3 | 14.5 | 37.6 |
| CV-3938 | 51.8 | — |
| OKY-046 | — | 86.4 |

The compounds according to the present invention used in Test Example 1 and Test Example 2 are shown in Table 2–1 and the control compounds in Table 2—2.

TABLE 2-1

| Compound | $R^2$ | $R^3$ | $R^1$ |
|---|---|---|---|
| Compound 1 | $CH_3$-CH($CH_3$)- | —$CO_2(CH_2)_3$-(3-pyridyl) | —$CO_2(CH_2)_3$-(3-pyridyl) |
| Compound 2 | $CH_3CH_2CH_2$— | —$CO_2(CH_2)_3$-(3-pyridyl) | —$CO_2(CH_2)_3$-(3-pyridyl) |
| Compound 3 | $CH_3CH_2CH_2$-CH($CH_3$)- | —$CO_2(CH_2)_3$-(3-pyridyl) | —$CO_2(CH_2)_3$-(3-pyridyl) |

TABLE 2-1-continued

| Compound | R² | R³ | R¹ |
|---|---|---|---|
| Compound 4 | (CH₃)₃C—CH₂— | —CO₂(CH₂)₃-(3-pyridyl) | —CO₂(CH₂)₃-(3-pyridyl) |
| Compound 8 | cyclohexyl | —CO₂(CH₂)₃-(3-pyridyl) | —CO₂(CH₂)₃-(3-pyridyl) |
| Compound 13 | isopropyl (CH₃)₂CH— | —COOCH₃ | —CO₂(CH₂)₃-(3-pyridyl) |
| Compound 15 | isopropyl (CH₃)₂CH— | —CO₂CH₂-(4-pyridyl) | —CO₂(CH₂)₃-(3-pyridyl) |
| Compound 28 | isopropyl (CH₃)₂CH— | —CO₂CH₂CH₂—N(piperazine)N—CH₂-(3-pyridyl) | —CO₂(CH₂)₃-(3-pyridyl) |
| Compound 30 | isopropyl (CH₃)₂CH— | —CO₂(CH₂)₄-(3-pyridyl) | —CO₂(CH₂)₄-(3-pyridyl) |

TABLE 2-2

| Compound | R² | R³ | R¹ |
|---|---|---|---|
| Control 1 | H | —CO₂(CH₂)₃-(3-pyridyl) | —CO₂(CH₂)₃-(3-pyridyl) |
| Control 2 | 2-nitrophenyl | —CO₂CH₂-(3-pyridyl) | —CO₂CH₂-(3-pyridyl) |
| Control 3 | 4-carboxyphenyl | —CO₂(CH₂)₃-(3-pyridyl) | —CO₂(CH₂)₃-(3-pyridyl) |
| CV-3988 | CH₂OCONHC₁₈H₃₇ / CH₃O—CH / CH₂OP(=O)(O⁻)—O—CH₂CH₂N⁺(thiazole) | | |
| OKY-046 | (imidazol-1-yl)CH₂—C₆H₄—CH=CH—COOH·HCl | | |

Test Example 3

In vitro test of action suppressing proliferation of cancer cells by concomitant use with doxorubicin Human rhinopharynx cancer derived KB cells (sensitive cells) and their multi-drug resistant clone VJ-300 cells (resistant cells) were used as the test cells. As the incubation solutions, use was made of 10% fetal calf serum (made by Flow Laboratories) and Eagle MEM medium (made by Nissui Seiyakusha) containing 0.292 mg/ml of L-glutamine (made by Flow Laboratories). The tests of the action in overcoming resistance to anti-cancer drugs or action reinforcing the effect of the anti-cancer drug through concomitant use of the anti-cancer drug doxorubicin (adriamycin, ADM) and the test compound were performed as follows: The test cells were suspended in incubation solutions and adjusted to a cell density of about 200 cells/ml. The cell suspensions were injected in 2 ml amounts into petri dishes and were incubated in a $CO_2$ gas incubator (5% $CO_2$, 95% air) at 37° C. for 24 hours. Next, 5 to 10 μl of a predetermined concentration of the aqueous ADM solution and a predetermined concentration of a DMSO solution of the test compound were added, then the incubation was continued for a further 7 days. After the end of the incubation, the result was immobilized by methanol, Giemsa stained and measured for the number of colonies per dish. The results were used to prepare a volume-reaction curve. From this, the ADM concentration of the a 50% cell survival rate ($LD_{50}$) was calculated and the effect in overcoming resistance to anti-cancer drugs and the effect in reinforcing the effect of anti-cancer drugs were judged. The results are shown in Table 3 using the concentration of $LD_{50}$ of ADM in the ADM alone group by KB cells as the resistance 1 and calculating the resistances of the following $LD_{50}$ concentrations as relative ratios. In Table 3, "ADM alone (control)" shows the group administered just ADM, "ADM+Compound 1" shows the group concomitantly administered the ADM and the Compound 1 (1 μg/ml) and, similarly below, "ADM+Compound 34" shows the group concomitantly administered the ADM and the Compound 34 (1 μg/ml). Further, as the control compounds, the results of using verapamil and nicardipine are shown in Table 3. In Table 3, "ADM+verapamil" shows the group concomitantly administered the ADM and verapamil (1 μg/ml) and, similarly below, "ADM+nicardipine" shows the group concomitantly administered the ADM and nicardipine (1 μg/ml).

TABLE 3

|  | Resistance with ADM | |
| --- | --- | --- |
|  | KB | VJ-300 |
| ADM alone (control) | 1 | 26.4 |
| ADM + Compound 1 | 0.6 | 3.4 |
| ADM + Compound 2 | 0.8 | 2.9 |
| ADM + Compound 3 | 0.6 | 1.9 |
| ADM + Compound 4 | 0.8 | 2.8 |
| ADM + Compound 5 | 0.5 | 2.5 |
| ADM + Compound 14 | 0.6 | 4.8 |
| ADM + Compound 15 | 0.8 | 6.2 |
| ADM + Compound 16 | 0.7 | 3.8 |
| ADM + Compound 17 | 0.7 | 4.4 |
| ADM + Compound 18 | 0.8 | 2.0 |
| ADM + Compound 19 | 0.8 | 5.0 |
| ADM + Compound 20 | 0.7 | 4.2 |
| ADM + Compound 21 | 1.1 | 3.9 |
| ADM + Compound 22 | 1.0 | 2.6 |
| ADM + Compound 23 | 0.8 | 1.2 |
| ADM + Compound 32 | 0.6 | 2.1 |
| ADM + Compound 33 | 1.2 | 4.9 |

TABLE 3-continued

|  | Resistance with ADM | |
| --- | --- | --- |
|  | KB | VJ-300 |
| ADM + Compound 34 | 1.2 | 0.9 |
| ADM + Verapamil | 0.7 | 4.8 |
| ADM + Nicardipine | 0.7 | 5.2 |

Test Example 4

In vitro test of action suppressing proliferation of cancer cells by concomitant use with vincristine The same method as in Test Example 3 was used to test the action of vincristine (VCR) on anti-cancer drugs, prepare a volume-reaction curve, and calculate the resistances. The results are shown in Table 4. In Table 4, "VCR alone (control)" shows the group administered with just VCR, "VCR+Compound 3" shows the group concomitantly administered VCR and the Compound 3 (1 μg/ml), and, the following similarly, "VCR+Compound 32" indicates the group concomitantly administered VCR and the Compound 32 (1 μg/ml). Further, "VCR+verapamil" shows the group concomitantly administered VCR and verapamil (1 μg/ml).

TABLE 4

|  | Resistance with VCR | |
| --- | --- | --- |
|  | KB | VJ-300 |
| VCR alone (control) | 1 | 603.4 |
| VCR + Compound 3 | 0.2 | 3.4 |
| VCR + Compound 4 | 0.4 | 22.2 |
| VCR + Compound 15 | 0.3 | 13.5 |
| VCR + Compound 16 | 0.4 | 11.8 |
| VCR + Compound 18 | 0.5 | 3.6 |
| VCR + Compound 19 | 0.9 | 7.3 |
| VCR + Compound 20 | 0.6 | 5.4 |
| VCR + Compound 21 | 0.7 | 4.9 |
| VCR + Compound 22 | 0.9 | 4.1 |
| VCR + Compound 23 | 0.1 | 13.1 |
| VCR + Compound 32 | 0.6 | 4.3 |
| VCR + verapamil | 0.3 | 39.6 |

Test Example 5

In vivo test of action suppressing proliferation of cancer cells by concomitant use with anti-cancer drug Effect for overcoming resistance to an anti-cancer drug for vincristine (VCR) resistant murine leukemia cell cancerous mice: $10^6$ VCR resistant murine leukemia (P388/VCR) cells were transplanted intraperitoneally into groups of six $CDF_1$ male mice, then the compound of the present invention (100 mg/kg) or control compound verapamil (60 mg/kg) or nicardipine (75 mg/kg) and VCR (100 μg/kg) were administered intraperitoneally for 5 days. The number of survival days were found and the life prolonging rate (T/C) with respect to the controls was found. The effect in overcoming resistance to an anti-cancer drug (T/V) was found by the following formula. The results are shown in Table 5. In Table 5, "Control" shows the group not administered VCR and the compound of the invention, "VCR alone" shows the group administered just VCR (100 μg/kg), "VCR+Compound 3" shows the group concomitantly administered the VCR (100 μg/kg) and the Compound 3 (100 mg/kg) and, similarly after this, "VCR+Compound 23" shows the group concomitantly administered the VCR (100

μg/kg) and the Compound 23 (100 mg/kg). Further, "VCR+ verapamil" shows the group concomitantly administered the VCR (100 μg/kg) and verapamil (60 mg/kg), while "VCR+ nicardipine" shows the group concomitantly administered the VCR (100 μg/kg) and nicardipine (75 mg/kg).

Effect for overcoming resistance to an anti-cancer drug (T/V) %

=[Life prolonging rate (T/C) in case of concomitant use of VCR and the compound of the present invention]/[Life prolonging rate (T/C) in case of VCR alone]×100

TABLE 5

|  | Mean days of survival (day) | Life prolonging rate T/C (%) | Effect for overcoming resistance T/V (%) |
| --- | --- | --- | --- |
| Control | 10.0 | 100 | — |
| VCR alone | 10.7 | 107 | 100 |
| VCR + Compound 3 | 17.2 | 172 | 161 |
| VCR + Compound 4 | 14.5 | 145 | 136 |
| VCR + Compound 11 | 13.7 | 137 | 128 |
| VCR + Compound 15 | 14.4 | 144 | 134 |
| VCR + Compound 23 | 13.2 | 132 | 123 |
| VCR + Verapamil | 13.6 | 136 | 127 |
| VCR + Nicardipine | 13.2 | 132 | 123 |

Test Example 6

Using Compound 18 to Compound 22 and Compound 32, the same procedure was followed as in Test Example 5 to find the effect for overcoming resistance to an anti-cancer drug in vincristine (VCR) resistant murine leukemia cell bearing mice. The results are shown in Table 6.

TABLE 6

|  | Mean days of survival (day) | Life prolonging rate T/C (%) | Effect for overcoming resistance T/V (%) |
| --- | --- | --- | --- |
| Control | 10.7 | 100 | — |
| VCR alone | 10.9 | 102 | 100 |
| VCR + Compound 18 | 15.3 | 143 | 140 |
| VCR + Compound 19 | 18.8 | 176 | 173 |
| VCR + Compound 20 | 15.8 | 148 | 150 |
| VCR + Compound 21 | 15.0 | 140 | 138 |
| VCR + Compound 22 | 15.8 | 148 | 150 |
| VCR + Compound 32 | 14.5 | 136 | 133 |

Test Example 7

Action easing KCl contraction in rat arteries

An approximately 2 mm long ring specimen was taken from the thoracic aorta of the rat and suspended in a Magnus tube filled with Krebs solution of 37° C. aerated with 95% $O_2$-5% $CO_2$. The specimen was stabilized for approximately 60 minutes, then a potassium chloride solution was added to the Magnus tube to give a final concentration of 50 μM. The positive control compound or the compound of the present invention was cumulatively added from $1 \times 10^{-10}$M to $1 \times 10^{-4}$M when the contraction reaction occurring at that time reached equilibrium. The contraction force was recorded by an FD-pickup (made by Nihon Kodensha) via a polygraph (made by Nihon Kodensha). The results are shown in Table 7 as the 50% inhibitory concentration ($IC_{50}$ value) of hyperpotassium contraction.

TABLE 7

| Positive control compound and compound of present invention | $IC_{50}$ value ($\times 10^{-7}$M) |
| --- | --- |
| Nicardipine | 5.3 |
| Verapamil | 23.5 |
| Nimodipine | 0.8 |
| Compound 1 | >300 |
| Compound 2 | >300 |
| Compound 4 | 205.0 |
| Compound 6 | 255.0 |
| Compound 7 | 130.0 |
| Compound 9 | 115.0 |
| Compound 10 | >300 |
| Compound 11 | >300 |
| Compound 12 | >300 |

Test Example 8

The same procedure was follows as in Test Example 7 to find the action for easing KCl contraction in rat aorta. The results are shown in Table 8 as the 50% inhibitory concentration ($IC_{50}$ value) of hypercalcemic contraction.

TABLE 8

| Positive control compound and compound of present invention | $IC_{50}$ value ($\times 10^{-7}$M) |
| --- | --- |
| Nicardipine | 1.5 |
| Compound 5 | 420 |
| Compound 13 | 57 |
| Compound 14 | 84 |
| Compound 15 | 42 |
| Compound 16 | 620 |
| Compound 18 | 46 |
| Compound 20 | 42 |
| Compound 21 | 70 |
| Compound 22 | 540 |
| Compound 32 | 105 |
| Compound 33 | 62 |

Test Example 9

Acute toxicity test

Animals used: ICR male mice (Charles River Japan) 7–8 weeks old, three mice per group.

Test method: The compound of the present invention was suspended in 0.5% sodium carboxymethylcellulose (CMC-Na) containing 0.1% Tween 80. It was administered to the mice intraperitoneally from 2000 mg/kg to 125 mg/kg by a ratio of ½ and from 125 mg/kg to 31.3 mg/kg by a ratio of $1/\sqrt{2}$ in groups of three mice until no more deaths were observed. The survival of the animals was observed up until 7 days after administration and the $LD_{50}$ was calculated by the Van Der Wearder area method.

The test results are shown below:

|  | $LD_{50}$ value |
| --- | --- |
| Compound 1 | 750 mg/kg |
| Compound 3 | 188 mg/kg |
| compound 5 | 1122 mg/kg |
| Compound 6 | 2000 mg/kg |
| Compound 16 | >2000 mg/kg |
| Compound 18 | >2000 mg/kg |

INDUSTRIAL APPLICABILITY

The compounds according to the present invention have a PAF antagonistic action and $TxA_2$ synthesis inhibiting action and have an action for improving allergies, inflammation, etc. Further, 1,4-dihydropyridine compounds according to the present invention reinforce the action of anti-cancer drugs when used concomitantly. The effects are particularly remarkable against cells acquiring resistance to anti-cancer drugs. For example, as clear from the above Table 4, human rhinopharynx cancer derived KB cell multi-drug resistant clone VJ-300 cells, compared with cells not acquiring resistance, required use of 603.4 times the concentration of the anti-cancer drug to obtain the same effect (50% cell survival rate), while with the concomitant use of the Compound 3 of the present invention (1 μg/ml), the same effect was obtained with 3.4 times the concentration.

Further, the compounds according to the present invention are low in toxicity and exhibit their effects in tests both in vitro and in vivo, and therefore, are useful as drugs for overcoming the resistance to anti-cancer drugs or drugs for reinforcing the effect of anti-cancer drugs.

We claim:

1. A 1,4-dihydropyridine compound or a salt thereof having the formula (I):

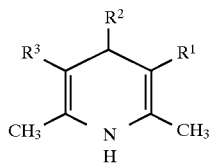

wherein; $R^1$ is —COO—A—(3-pyridyl), where A is a $C_3$–$C_6$ straight chain alkylene group or a $C_3$–$C_6$ straight chain alkylene group in which a piperazine ring is interposed at both nitrogen atoms of the piperazine ring in the chain; $R^2$ is a $C_2$–$C_{10}$ alkyl, alkenyl or alkynyl group, a $C_1$–$C_4$ alkyl or alkenyl group substituted with a phenyl, furyl or cycloalkyl group, $C_3$–$C_6$ cycloalkyl group, or a $C_3$–$C_6$ cycloalkyl group substituted with a alkynyl group; and $R^3$ is the same as $R^1$ or —COO—$R^4$, where $R^4$ is a $C_1$–$C_4$ alkyl group or a $C_1$–$C_4$ alkyl group substituted with a cyano, an amino, a N-methyl-N-benzylamino, a phenyl, a phenylthio, or a heterocyclic group having a nitrogen atom and selected from the group consisting of a pyridyl, a pyridyloxy, a alkyl substituted piperazino group, an indolyl, a aziridinyl, a tetrahydropyridyl and a thiazolyl group.

2. The 1,4-dihydropyridine compound or salt thereof of claim 1, wherein A of $R^1$ is a trimethylene group, a tetramethylene group, a $C_3$–$C_4$ straight chain alkylene group or a $C_3$–$C_4$ straight alkylene group in which a piperazine ring is interposed at both nitrogen atoms of the piperazine ring in the chain.

3. The 1,4-dihydropyridine compound or salt thereof of claim 2, wherein A of $R^1$ is a trimethylene group.

4. The 1,4-dihydropyridine compound or salt thereof of claim 1, wherein $R^3$ is the same as $R^1$.

5. The 1,4-dihydropyridine compound or salt thereof of claim 1, wherein $R^3$ is —COO—$R^4$.

6. The 1,4-dihydropyridine compound or salt thereof of any one of claims 1 to 5, wherein $R^2$ is a $C_3$–$C_9$ alkyl, alkenyl or alkynyl group; a $C_1$–$C_4$ alkyl or alkenyl group substituted with a phenyl, furyl or cycloalkyl group; or a $C_3$–$C_6$ cycloalkyl group.

7. The 1,4-dihydropyridine compound of claim 6, wherein $R^2$ is n-propyl, isopropyl, n-butyl, n-pentyl, n-hexyl, n-heptyl, n-octyl, 1-methylpropyl, 2-methylpropyl, 1-methylbutyl, 1-ethylpropyl, 1-ethylpentyl, 2,2-diemthylpropyl, 2,4,4-trimethylpentyl, 2-methyl-1-propenyl, 2,6-dimethyl-5-heptenyl, 1-heptynyl, 3,3-dimethylcyclohexylmethyl, benzyl or cyclohexyl.

8. A pharmaceutical composition comprising an effective amount of a compound, or a pharmacologically acceptable salt thereof, of claim 1 and a pharmaceutically acceptable carrier.

9. A method for treating resistance to anticancer drugs which comprises administering to a person in need thereof, an effective amount of a compound, or a pahrmacologically acceptable salt thereof, of claim 1 as the active ingredient.

* * * * *

UNITED STATES PATENT AND TRADEMARK OFFICE
CERTIFICATE OF CORRECTION

PATENT NO. : 5,843,950
DATED : December 1, 1998
INVENTOR(S) : Shigeyuki TASAKA et al.

It is certified that error appears in the above-indentified patent and that said Letters Patent is hereby corrected as shown below:

Title Page, Item [75], in the Inventors, line 1, "Saitama" should read --Omiya--.

Claim 7, Col. 24, line 26-27, "2,2-diemthylpropyl" should read --2,2-dimethylpropyl--.

Claim 9, Col. 24, line 36, "pahrmacologically" should read --pharmacologically--.

Signed and Sealed this

Third Day of August, 1999

Attest:

Attesting Officer

Q. TODD DICKINSON

Acting Commissioner of Patents and Trademarks